United States Patent [19]
Marhold et al.

[11] Patent Number: 6,137,011
[45] Date of Patent: Oct. 24, 2000

[54] PROCESS FOR THE PREPARATION OF BISTRIFLUOROMETHYLBENZYLAMINES

[75] Inventors: Albrecht Marhold, Leverkusen; Ernst Kysela, Bergisch Gladbach, both of Germany

[73] Assignee: Bayer Aktiengesellschaft, Leverkusen, Germany

[21] Appl. No.: 09/513,088

[22] Filed: Feb. 25, 2000

[30] Foreign Application Priority Data

Mar. 2, 1999 [DE] Germany .................. 199 08 943

[51] Int. Cl.⁷ .................................................. C07C 209/00
[52] U.S. Cl. .......................................... 564/407; 564/415
[58] Field of Search ..................... 564/407, 415

[56] References Cited

PUBLICATIONS

Database Chemabs Online!, Chemical Abstracts Service, Columbus, Ohio, US, Uehara, Ryoichi et al: "Cobalt Catalyst" retrieved from STN Database accession No. 92:100139, XP002133412, *Zusammenfassung* & JP 54 037593 B (Nikko Scientific and Chemical Industries, Ltd., Japan) Nov. 15, 1979.

Database WPI, Section Ch, Week 198729, Derwent Publications Ltd., London, GB; Class B05, AN 1987–202004, XP002133413 & JP 62 129257 A (Daicel Chem Ind Ltd), Jun. 11, 1987 *Zusammenfassung*.

J.A.C.S., vol. 66, May 1944, Frank C. Whitmore et al, Basically Substituted Aliphatic Nitriles and Their Catalytic Reduction to Amines—p. 725.

J.A.C.S., vol. 82, (month unavailable) 1960, p. 2386, Morris Freifelder, A Low Pressure Process for the Reduction of Nitriles. Use of Rhodium Catalyst.

Chem. Ber. , vol. 85, pp. 324–327, (month unavailable) 1965, Jan Thesing und Felix Schülde: Notiz über die präparative Darstellung von Heteroauzin und Tryptamin.

J. Pharm. Sci., vol. 54, p. 1204, (month unavailable) 1965, Freifelder et al Preparation of Isomeric Trifluoromethylbenzylamines.

*Primary Examiner*—Samuel Barts
*Attorney, Agent, or Firm*—Joseph C. Gil; Diderico van Eyl

[57] ABSTRACT

Bistrifluoromethylbenzylamines are obtained in a simple manner in high purities and with good yields by catalytic hydrogenation of the corresponding bistrifluoromethylbenzonitriles if the process is carried out in the presence of Raney cobalt, at least one aliphatic ether and ammonia.

8 Claims, No Drawings

PROCESS FOR THE PREPARATION OF BISTRIFLUOROMETHYLBENZYLAMINES

FIELD OF THE INVENTION

The present invention relates to an improved process for the preparation of bistrifluoromethylbenzylamines by hydrogenation of the corresponding bistrifluoromethylbenzonitriles.

BACKGROUND OF THE INVENTION

Bistrifluoromethylbenzylamines and, in particular, 3,5-bistrifluoromethylbenzylamine are important as crop-protection and pharmaceutical active ingredients and as precursors therefor.

Earlier literature (see J. A. C. S. 66, 725 (1944) and 82, 2386 (1960)) and Chem. Ber. 85, 325 (1952) describe how aliphatic nitriles and indolylacetonitriles can be converted into the corresponding amines by catalytic reduction with hydrogen in the presence of Raney nickel or rhodium. If any solvents at all are used, these are alcohols. If necessary, it is possible to carry out the process in the presence of ammonia.

For the preparation of trifluoromethylbenzylamines, the catalytic reduction of trifluoromethylbenzonitriles in the presence of rhodium or palladium catalysts, ethanol and hydrogen chloride is described, where the amines are produced as hydrochloride. These hydrochlorides must be purified in a complex manner and then be converted into the free amines (see J. Pharm. Sci. 54, 1204 (1965)).

According to U.S. Pat. No. 3,726,969, the last-named process is also used for the preparation of 3,5-bistrifluoromethyl-benzylamine. Here too, complex purification steps have to be undertaken. According to this process, only the amine hydrochloride, and not the free amine, has been prepared.

There is therefore still a need for a process for the preparation of bistrifluoromethylbenzylamines in which the free amines are obtained in high purities in a simple manner.

SUMMARY OF THE INVENTION

The invention, meeting the above-named need, is directed to a process for the preparation of bistrifluoromethylbenzylamines by catalytic hydrogenation of the corresponding bistrifluoromethylbenzonitriles, which is characterized in that the process is carried out in the presence of Raney cobalt, at least one aliphatic ether and ammonia. These and other features, aspects, and advantages of the present invention will become better understood with reference to the following description and appended claims.

DESCRIPTION OF THE INVENTION

In the process according to the invention, it is possible, for example, to use bistrifluoromethylbenzonitriles of the formula (I)

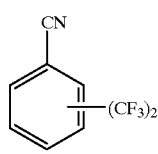

and to prepare bistrifluoromethylbenzylamines of the formula (II)

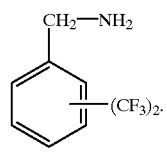

Preference is given to using bistrifluoromethylbenzonitriles of the formula (III)

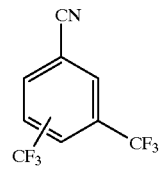

and preparing bistrifluoromethylbenzylamines of the formula (IV)

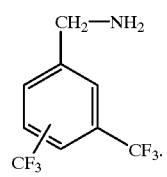

Particular preference is given to using 3,5-bistrifluoromethyl-benzonitrile and to preparing 3,5-bistrifluoromethylbenzylamine.

Bistrifluoromethylbenzonitriles are either commercially available or can be prepared in a known manner or analogously there too.

Raney cobalt is likewise commercially available or can be obtained in a known manner from an aluminium-cobalt alloy by leaching out the aluminium using aqueous alkalis.

The aliphatic ethers can be linear, branched or cyclic and contain, for example, from 4 to 10 carbon atoms, such as diethyl, diisopropyl, methyl tert-butyl, dibutyl, ethylene glycol dimethyl, diethylene glycol dimethyl and tetraethylene glycol dimethyl ethers, and tetrahydrofuran, 2-methyltetrahydrofuran and dioxane. It is also possible to use mixtures of two or more aliphatic ethers.

Per kg of bistrifluoromethylbenzonitrile, it is possible to use, for example, from 0.3 to 2 kg of aliphatic ethers and from 0.05 to 1 kg of Raney cobalt (calculated as metal). These amounts are preferably from 0.5 to 1.2 kg of aliphatic ethers and from 0.07 to 0.2 kg of Raney cobalt.

The ammonia should be largely dry and can be used in commercially available form (purities 99.5% or higher). It can be conveyed to the reaction vessel in liquid form or gaseous form. Per kg of bistrifluoromethylbenzonitrile, it is possible, for example, to use from 0.2 to 4 kg of ammonia. This amount is preferably from 0.3 to 2.5 kg.

The process according to the invention can, for example, be carried out at from 50 to 150° C. and a hydrogen pressure of from 20 to 200 bar. Preference is given to temperatures of from 70 to 110° C. and pressures of from 30 to 150 bar.

It is advantageous to carry out the hydrogenation according to the invention until all of the bistrifluoromethylbenzonitrile has reacted. This can be checked, for example, using GC. Generally, complete conversion of the bistrifluoromethylbenzonitrile is achieved after from 3 to 15 hours.

The procedure for a preferred embodiment of the process according to the invention is as follows. The bistrifluoromethylbenzonitrile, the aliphatic ether and the Raney cobalt are initially introduced into a pressure vessel, and then an inert gas, e.g., nitrogen, is passed through the pressure vessel in order to displace oxygen which is present. The pressure vessel is then closed, firstly the ammonia is added, and finally hydrogen is injected, and the mixture is heated to the proposed reaction temperature. It is also possible to top up the bistrifluoromethylbenzonitrile and ammonia during the hydrogenation and to continue the hydrogenation in this way. Work-up of the mixture which is present at the end of the reaction can be carried out in a simple manner, for example by firstly cooling the reaction vessel, e.g., to from 20 to 50° C., and then allowing the ammonia to evaporate by releasing the pressure. If desired, it is possible to recover the ammonia, e.g., by cooling, and reuse it in the next batch. Then, the catalyst can be removed, e.g., by filtration. The catalyst too can be reused. Finally, the catalyst-free mixture can be distilled, where the aliphatic ether used as solvent passes over first and can likewise be reused. By fractionation at reduced pressure, e.g., at from 10 to 100 mbar, it is possible, finally, to isolate the prepared free bistrifluoromethylbenzylamine in purities greater than 99% and in yields of in most cases greater than 80%.

Using the process according to the invention it is possible to obtain bistrifluoromethylbenzylamines in a simple and effective manner directly in free form and in high purities. The primary preparation of bistrifluoromethylbenzylamine hydrochlorides and complex purification procedures in this stage are not necessary.

It is extremely surprising that the procedure according to the invention produces these advantages. To date, the solvents used for such hydrogenations were exclusively alcohols and, specifically for the preparation of trifluoromethylbenzylamines, only noble metal catalysts in the presence of hydrogen chloride.

When, by 1960, Raney nickel catalysts in the presence of ammonia and alcohols as solvent were also considered for the hydrogenation of aliphatic nitrites, the development of the hydrogenation of trifluoro-methylbenzylamines then took another direction, namely towards noble metal catalysts in the presence of hydrogen chloride and, as before, alcohols as solvents. It was therefore not obvious to consider the use of Raney cobalt in the presence of ammonia or using other solvents for improving the known preparation process for bistrifluoromethylbenzyl-amines.

In the process according to the invention, not only is the use of Raney cobalt catalysts an essential feature, but also the use of aliphatic ethers. Hitherto, aliphatic ethers have not been considered for either the hydrogenation of aliphatic nitrites or the hydrogenation of trifluoromethylbenzonitriles. As can be seen from Comparative Example 1, the combination of Raney cobalt catalyst, alcohol as solvent in the presence of ammonia produces entirely unsatisfactory results, namely a reaction mixture, of which only around 30% consists of the desired bistrifluoromethylbenzylamine, but consists of far more than 50% undesired bistrifluoromethylbenzyl-bistrifluoromethylbenzamidate. This comparative example clearly shows the unexpected positive effect associated with the use according to the invention of aliphatic ethers as solvent.

The invention is further illustrated but is not intended to be limited by the following examples in which all parts and percentages are by weight unless otherwise specified.

EXAMPLES

Example 1

500 g of 3,5-bistrifluoromethylbenzonitrile, 300 ml of liquid ammonia, 300 ml of tetrahydrofuran and 50 g of Raney cobalt were initially introduced into an autoclave, and then hydrogen was injected for 10 hours at 90° C. to a pressure of 115 bar. The system was then firstly cooled to 22° C. and decompressed via a scrubber, the ammonia evaporating off. The catalyst was filtered off with suction, the mixture was concentrated and the residue was fractionated via a Vigreux column under reduced pressure. At a pressure of 50 mbar and a temperature of from 102 to 105° C., 356 g (70% of theory) of 3,5-bistrifluoromethylbenzylamine having a purity of 99.4% (GC, area %) passed over. Collected as tailings at 20 mbar were a further 14 g of 90% pure product. 88 g of distillation residue were left behind.

The tailings were added to the distillation of the next batch and thus a total of 90% of the theoretical amount of bistrifluoromethylbenzylamine were obtained in greater than 99% purity.

Example 2

Analogously to Example 1, 100 g of 3,5-bistrifluoromethyl-benzonitrile, 300 ml of liquid ammonia, 100 ml of tetrahydrofuran and 50 g of Raney cobalt were initially introduced. Hydrogen was injected for 5 hours under the same conditions, and the mixture was worked up as described. This gave 84 g (83% of theory) of 3,5-bistrifluoromethylbenzyl-amine with a purity of 99.6% (GC, area %) and a residue of 3 g.

Example 3

40 kg of 3,5-bistrifluoromethylbenzonitrile, 20 kg of tetrahydrofuran and 4.0 kg of Raney cobalt were initially introduced into a 120 l stirred autoclave and, after flushing with nitrogen, 23 kg of ammonia were injected. Hydrogen was then injected to a pressure of 30 bar, the mixture was heated to 90° C. and further hydrogen was injected to a pressure of from 110 to 120 bar. After 12 hours, a sample was taken and tested for complete conversion using GC. If conversion was incomplete, hydrogenation was continued under the above conditions until the conversion was complete. After complete conversion, the system was firstly cooled to 20° C. and decompressed via a scrubber, the ammonia evaporating off. The catalyst was then filtered off, the autoclave and the filter cake were rinsed with 10 kg of tetrahydrofuran and the filtrate combined with the rinse liquid was concentrated on a rotary evaporator. The crude product solutions from 3 batches (for details see the table below) concentrated in this way were then combined and distilled.

| Batch | Amount (kg) | Content of 3,5-bistrifluoro-methylbenzylamine (GC, area % %) | 3,5-Bistrifluoromethyl-benzylamine (kg) |
| --- | --- | --- | --- |
| 3-1 | 59.2 | 60.63 | 35.89 |
| 3-2 | 58.6 | 57.80 | 33.87 |
| 3-3 | 60.0 | 59.85 | 35.91 |

Batch 3-2 was obtained from 39.5 kg of 3,5-bistrifluoromethylbenzonitrile.

The distillation was carried out via a column 2 m in height and 100 mm in diameter, which was packed with 7×7 mm Wilson spirals. At a reflux ratio of 1:6, a head temperature of from 90 to 92° C. and a pressure of 36 mbar, a total of 102 kg of 3,5-bistrifluoromethylbenzylamine were obtained in 5 fractions having purities from 99.55 to 99.75% (GC, area %), which corresponds to a yield of 84% of theory.

Example 4

Analogously to Example 1, 100 g of 2,4-bistrifluoromethyl-benzonitrile, 200 ml of liquid ammonia, 150 ml of tetrahydrofuran and 30 g of Raney cobalt were initially introduced, then hydrogen was injected to a pressure of 120 bar at 100° C.

Analogous work-up gave 75 g (74.4%) of 2,4-bistrifluoromethylbenzyl-amine having a boiling point of 78° C./10 mbar, $n^D_{20}$:1.4280.

Comparative Example
(Solvent alcohol instead of ether)

500 g of 3,5-bistrifluoromethylbenzonitrile, 300 ml of liquid ammonia, 300 ml of methanol and 25 g of Raney cobalt were initially introduced into an autoclave and hydrogenated with hydrogen for 12 hours at 90° C. and 115 bar. Prior to work-up, the system was firstly cooled and decompressed via a scrubber, the ammonia evaporating off. The catalyst was filtered off and the mixture was concentrated. According to GC-MS analysis, the crude product contained only 31 area % of 3,5-bistrifluoromethylbenzylamine, but 56 area % of N-3,5-bistrifluoromethylbenzyl-3,5-bistrifluoromethylbenzamidate. The distillation at 3 mbar up to a reboiler temperature of 170° C. gave 43 g of distillate and 351 g of residue were left behind. The distillate contained 3,5-bistrifluoromethylbenzylamine in an amount corresponding to 8% of theory (calculated on the basis of 100% pure product).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a bistrifluoromethylbenzyl-amine comprising the step of catalytically hydrogenatining a bistrifluoromethylbenzonitrile, wherein the process is carried out in the presence of a Raney cobalt, at least one aliphatic ether, and ammonia.

2. The process according to claim 1, wherein the bistrifluoromethylbenzonitrile used is of the formula (I)

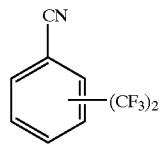

(I)

and the bistrifluoromethylbenzylamine prepared is of the formula (II)

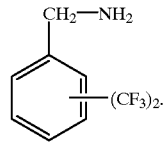

(II)

3. The process of claim 1, wherein the aliphatic ethers comprise a member selected from the group consisting of linear, branched and cyclic ethers having from 4 to 10 carbon atoms.

4. The process of claim 1, wherein from 0.3 to 2 kg of aliphatic ethers are used per kg of bistrifluoromethylbenzonitrile.

5. The process of claim 1, wherein from 0.05 to 1 kg of Raney cobalt is used per kg of bistrifluoromethylbenzonitrile.

6. The process of claim 1, wherein from 0.2 to 4 kg of ammonia are used per kg of bistrifluoromethyl-benzonitrile.

7. The process of claim 1, wherein the process is carried out at a temperature ranging from about 50 to 150° C. and a hydrogen pressure ranging from about 20 to 200 bar.

8. The process of claim 1, wherein the mixture present at the end of the reaction is worked up by firstly cooling the reaction vessel, then allowing the ammonia to evaporate by releasing the pressure, then removing the catalyst and finally distilling the catalyst-free mixture.

* * * * *